(12) United States Patent
Silbermann

(10) Patent No.: US 12,727,740 B2
(45) Date of Patent: Sep. 8, 2026

(54) ENDOSCOPE

(71) Applicant: AMBU A/S, Ballerup (DK)

(72) Inventor: Victor Silbermann, Them (DK)

(73) Assignee: AMBU A/S, Ballerup (DK)

( * ) Notice: Subject to any disclaimer, the term of this patent is extended or adjusted under 35 U.S.C. 154(b) by 109 days.

(21) Appl. No.: 18/693,496

(22) PCT Filed: Sep. 22, 2022

(86) PCT No.: PCT/EP2022/076398
§ 371 (c)(1),
(2) Date: Mar. 19, 2024

(87) PCT Pub. No.: WO2023/052237
PCT Pub. Date: Apr. 6, 2023

(65) Prior Publication Data

US 2024/0423451 A1 Dec. 26, 2024

(30) Foreign Application Priority Data

Sep. 28, 2021 (DK) ............................ PA202170473

(51) Int. Cl.
*A61B 1/00* (2006.01)

(52) U.S. Cl.
CPC ...... *A61B 1/00068* (2013.01); *A61B 1/00128* (2013.01)

(58) Field of Classification Search
CPC . A61B 1/00068; A61B 1/00128; A61B 1/015; A61B 1/126
See application file for complete search history.

(56) References Cited

U.S. PATENT DOCUMENTS 4,537,182 A 8/1985 Otani
4,562,830 A 1/1986 Yabe
(Continued)

FOREIGN PATENT DOCUMENTS

CN 202908666 U 5/2013
CN 107080515 A 8/2017
(Continued)

OTHER PUBLICATIONS

Search report in Danish Patent Application No. PA 2021 70473, dated Feb. 24, 2022, 9 pages.
(Continued)

*Primary Examiner* — Timothy J Neal
(74) *Attorney, Agent, or Firm* — Faegre Drinker Biddle & Reath LLP

(57) ABSTRACT

An endoscope including a handle and an insertion cord. The handle includes a first handle housing part and a valve and suction connector assembly. The valve and connector assembly including a suction connector part (11), a valve housing main body (100), a plunger (101) and a valve housing lid (102). The valve housing lid (102) includes an entry pipe (107) connected to a suction channel tube in fluid communication with a suction port at the distal end of the insertion cord. The valve housing main body (100) includes an exit pipe (104) connected to said suction connector part (11). The suction connector part (11) is accommodated in the wall of the handle housing part and includes an oblong engagement flange in frictional engagement with said wall.

20 Claims, 9 Drawing Sheets

(56) References Cited

U.S. PATENT DOCUMENTS

Figure 1:
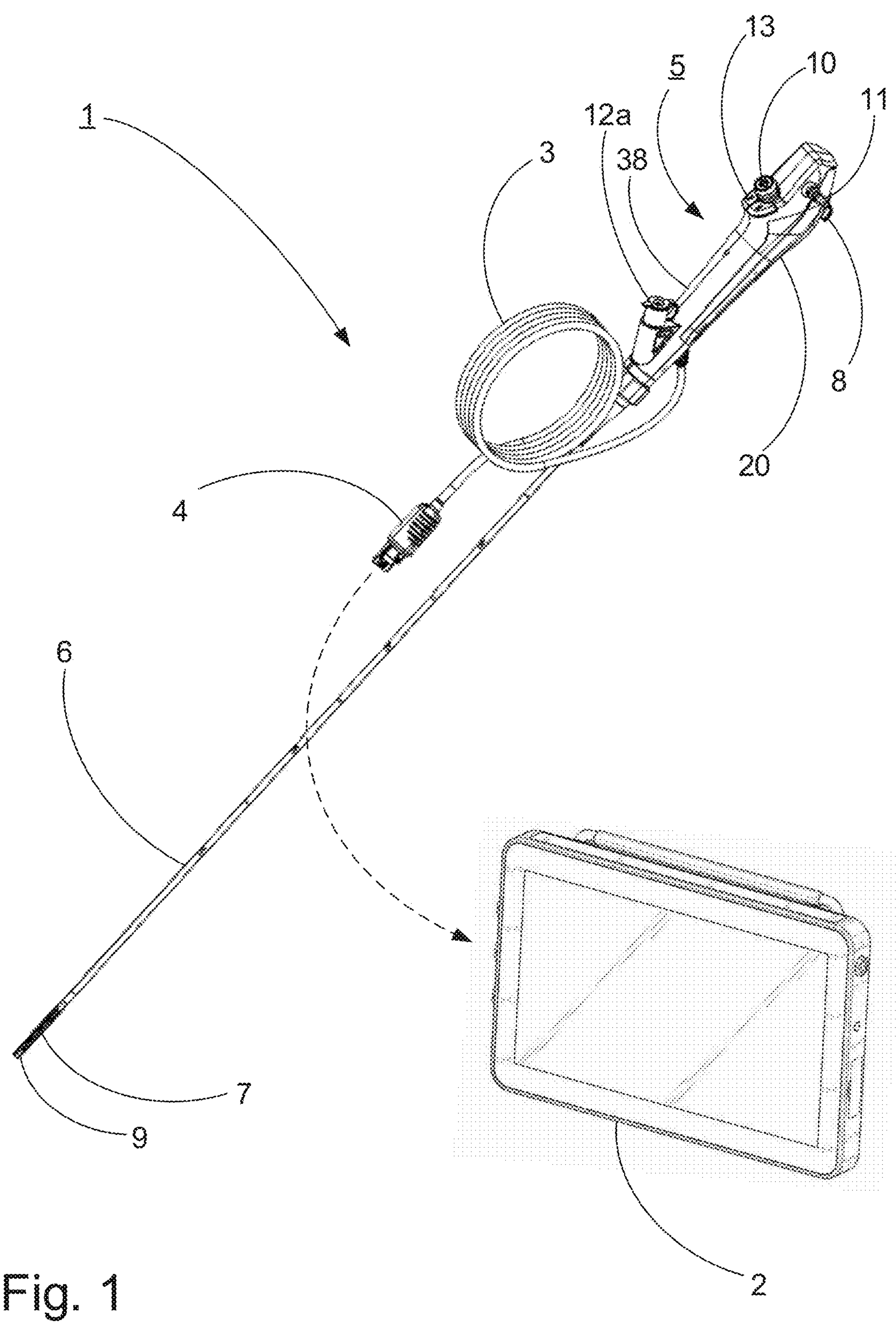

| | | | | |
|---|---|---|---|---|
| 8,414,478 | B2 | 4/2013 | Yamane | |
| 8,491,468 | B2 | 7/2013 | Yamane | |
| 8,568,303 | B2 | 10/2013 | Yamane | |
| 8,840,545 | B2 | 9/2014 | Watanabe | |
| 9,968,241 | B2 | 5/2018 | Iuel | |
| 2012/0071844 | A1* | 3/2012 | Yamane | A61B 1/00068 604/319 |
| 2019/0350440 | A1* | 11/2019 | Leong | A61B 1/0057 |
| 2020/0016637 | A1 | 1/2020 | Still et al. | |
| 2023/0038305 | A1 | 2/2023 | Hallauer et al. | |

FOREIGN PATENT DOCUMENTS

| | | | |
|---|---|---|---|
| EP | 0182443 | A2 | 5/1986 |
| EP | 2441379 | B1 | 11/2016 |
| JP | 2008228990 | A | 10/2008 |
| JP | 4841278 | B2 | 12/2011 |
| JP | 2012075473 | A | 4/2012 |
| JP | 5602712 | B2 | 10/2014 |
| WO | 2018/162559 | A1 | 9/2018 |

OTHER PUBLICATIONS

International Search Report and Written Opinion received for PCT Patent Application No. PCT/EP2022/076398, mailed on Dec. 1, 2023, 10 pages.

* cited by examiner

ENDOSCOPE

CROSS-REFERENCE TO RELATED APPLICATIONS

This application is a National Stage entry under 35 U.S.C. § 371 of International Application No. PCT/EP2022/076398, filed Sep. 22, 2022, which claims priority from and the benefit of Danish Patent Application No. PA 2021 70473, filed Sep. 28, 2021; the disclosures of said applications are incorporated by reference herein in their entirety.

The present disclosure relates to endoscopes, more specifically but not exclusively to disposable endoscopes with a suction valve assembly.

It is well known to provide medical endoscopes with suction facilities allowing liquid to be sucked through the working channel or a dedicated suction channel. For this, the endoscope comprises a suction connector connectable to a vacuum source normally available in hospitals and other medical settings. The endoscope further comprises a valve means which may upon activation by the operator connect the working channel or the suction channel to the vacuum source.

Traditionally, the valve and suction connector have been provided as a disposable unit externally attachable to a reusable endoscope by means of a suitable receptacle, e.g. as disclosed in U.S. Pat. No. 8,840,545.

With the advent of disposable endoscopes, the need for a separate disposable unit is less pronounced as the valve and suction connector may just as well be integrated in the disposable endoscope. One such integrated valve and suction connector assembly is disclosed in CN107080515.

In both of U.S. Pat. No. 9,968,241 and WO2018/162559 the suction connector is held in a receptacle provided in the handle housing wall of an endoscope and secured with screws. No details of the valves are given.

Integrating the valve and suction connector in a disposable endoscope, the constituent parts need to be few, have low cost in manufacture and easy to assemble to keep the production time and costs down, yet still be reliable. Moreover, the valve and connector assembly needs to find room in the already sparse volume within the handle of the endoscope.

Based on this it is the object of the present disclosure to provide a valve and suction connector assembly that facilitates the assembly of a disposable endoscope and provides for suction through the insertion cord of an endoscope.

According to a first aspect of the disclosure this object is achieved by an endoscope comprising a handle and an insertion cord, said first handle housing part having a wall with an internal wall surface defining the interior of the handle, and an external wall surface, the internal wall surface and the external wall surface being interconnected by a valve accommodation passage, and said valve and connector assembly comprising a suction connector part, a valve housing main body, a plunger, and a valve housing lid, wherein said valve housing main body is accommodated in said valve accommodation passage so as to extend from the interior of the handle through said valve accommodation passage and beyond said external wall surface, and wherein the plunger is so accommodated in the valve housing main body that the plunger extends from the interior of the handle through said valve accommodation passage and beyond said external wall surface.

This facilitates the easy accommodation of the valve housing of the valve and suction connector assembly in the housing during assembly.

According to an embodiment, the plunger extends further beyond the external wall surface than the valve housing main body. This makes the plunger easy to mount during assembly and allows for the use of the valve cap as a push-button and for biasing the plunger into engagement with the valve seat in the inactivated position.

According to an embodiment, the valve housing main body comprises a valve cap engagement surface. This allows the valve cap to be easily mounted on and from the exterior side of the handle during assembly, this is in particular the case when according to a further embodiment, the valve cap engagement surface comprises a flange. This flange may then grip and engage behind an inward projection of the valve cap, such as an inner circumferential bead.

According to an embodiment, the plunger comprises a valve cap engagement flange adapted to retain a valve cap in engagement with the plunger. This allows a valve cap to engage and bias the plunger into the inactivated position, where the sealing member engages the valve seat.

According to an embodiment, the valve housing lid comprises an entry pipe connected to a suction channel tube in fluid communication with a suction port at the distal end of the insertion cord, the valve housing main body comprises an exit pipe connected to said suction connector part, and the suction connector part is accommodated in said wall and said suction connector part comprises an oblong engagement flange in frictional engagement with said wall. This allows for simple insertion and positioning of the valve and suction connector assembly as oblong engagement flange allows the simple securing of the suction connector part to the handle housing by a turning motion, this turning motion furthermore serving to swing the valve and suction connector assembly into the correct mounting position with respect to the handle housing part.

According to an embodiment, the valve housing main body comprises at least one pair of laterally extending elastic tabs retained in position by cam surfaces provided on the internal wall surface. These elastic tabs aid in the alignment with the aperture provided for the valve assembly in the handle housing part and at least temporarily allows the valve assembly to be held in place, e.g. during the curing of an adhesive, when adhering the valve housing main body to the handle housing part.

According to an embodiment, said elastic tabs are themselves further secured in position by an adhesive provided between said elastic tabs and the internal wall surface. This adds to the number of points where the two parts are secured with respect to each other.

According to an embodiment, the valve housing lid is adhered to said valve housing main body. Providing a valve housing lid and valve housing main body as separate items and then securing them mutually by means of adhesive, simplifies the manufacturing of the individual parts by e.g. injection moulding while still providing simply assembly.

According to an embodiment, the valve housing comprises a valve seat surface and said plunger comprises a sealing member adapted to engage said valve seat surface. This provides for a simple valve mechanism which is easy to mount from the outside of the endoscope.

According to an embodiment, said sealing member is biased towards engagement with said valve seat by an elastomeric valve cap providing a push-button valve cap arranged on the exterior of said first handle housing part. This provides for a simple return mechanism not necessitating the use of separate additional springs or the like.

According to an embodiment, the sealing member is an O-ring of an elastomer material. This is a simple and efficient way of providing the seal and moreover renders itself for the introduction from the outside via the central passage of the valve housing main body.

According to an embodiment, the plunger comprises a passage in fluid communication with the exterior of the handle housing. This provides a simple means for idle suction from the external vacuum source when the push-button valve cap is not depressed.

According to a second aspect the object of the disclosure is also achieved by a system comprising a display device and an endoscope according to any one of the preceding claims connectable to said display device.

Figure 2:
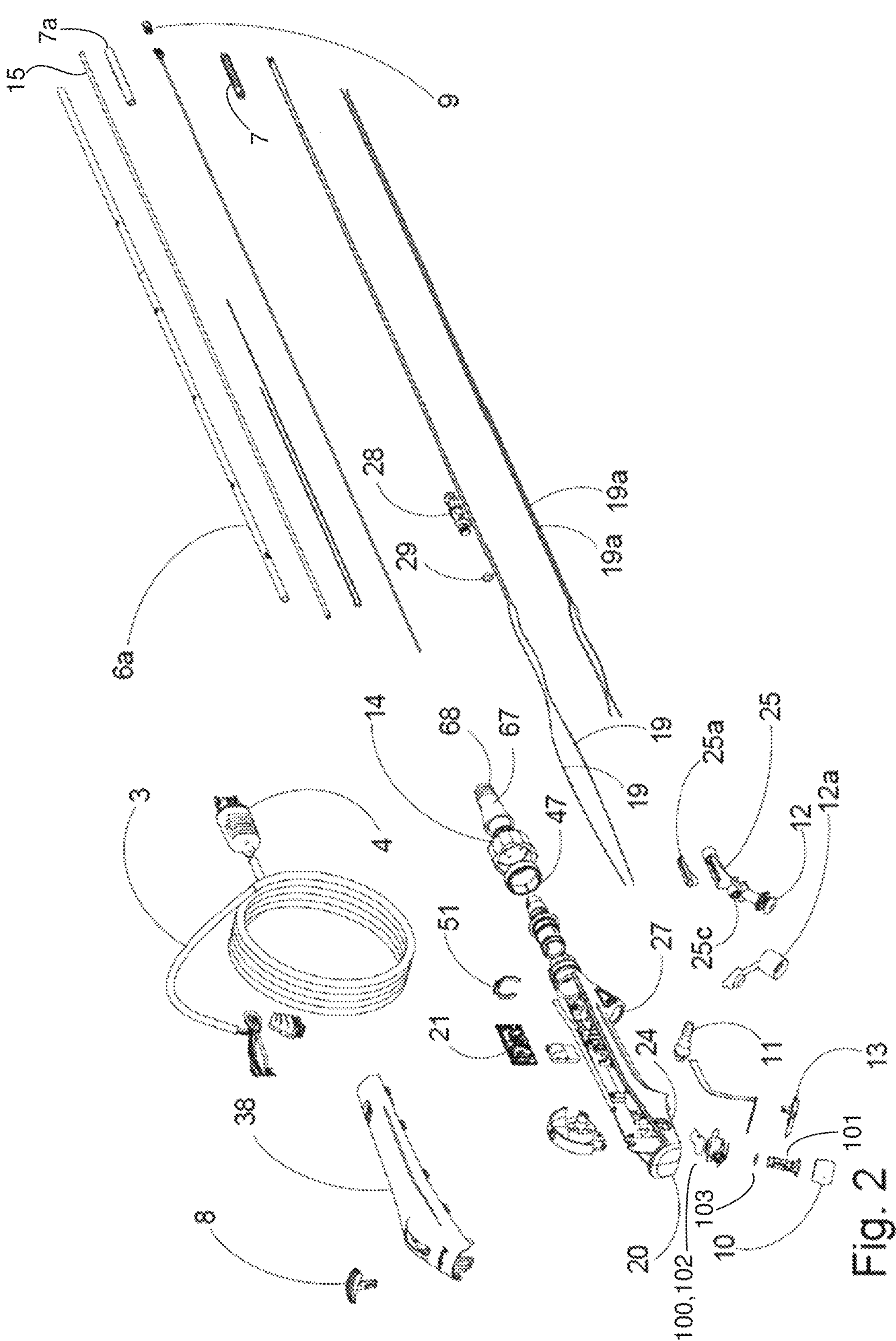
Figure 3:
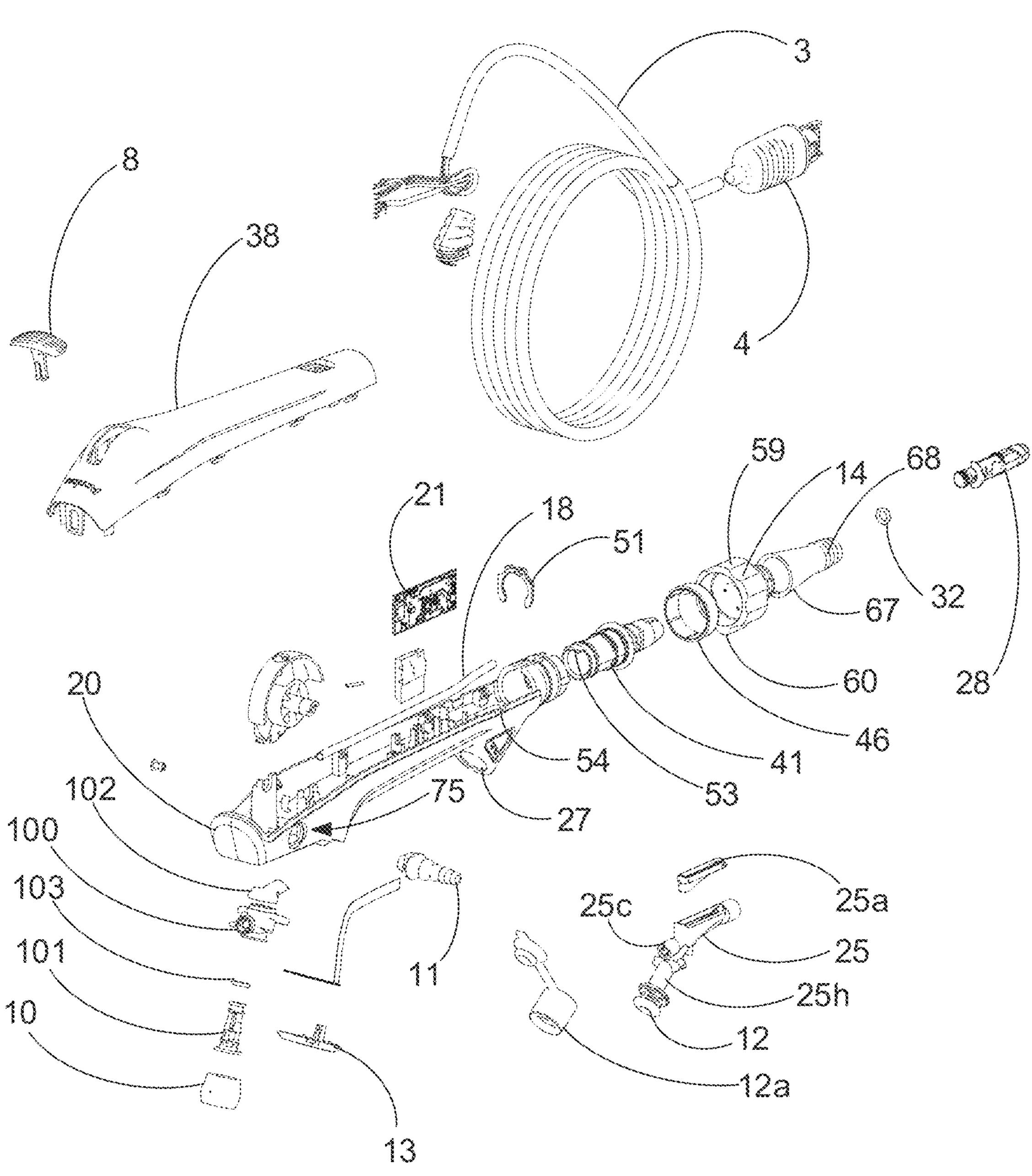
Figure 4:
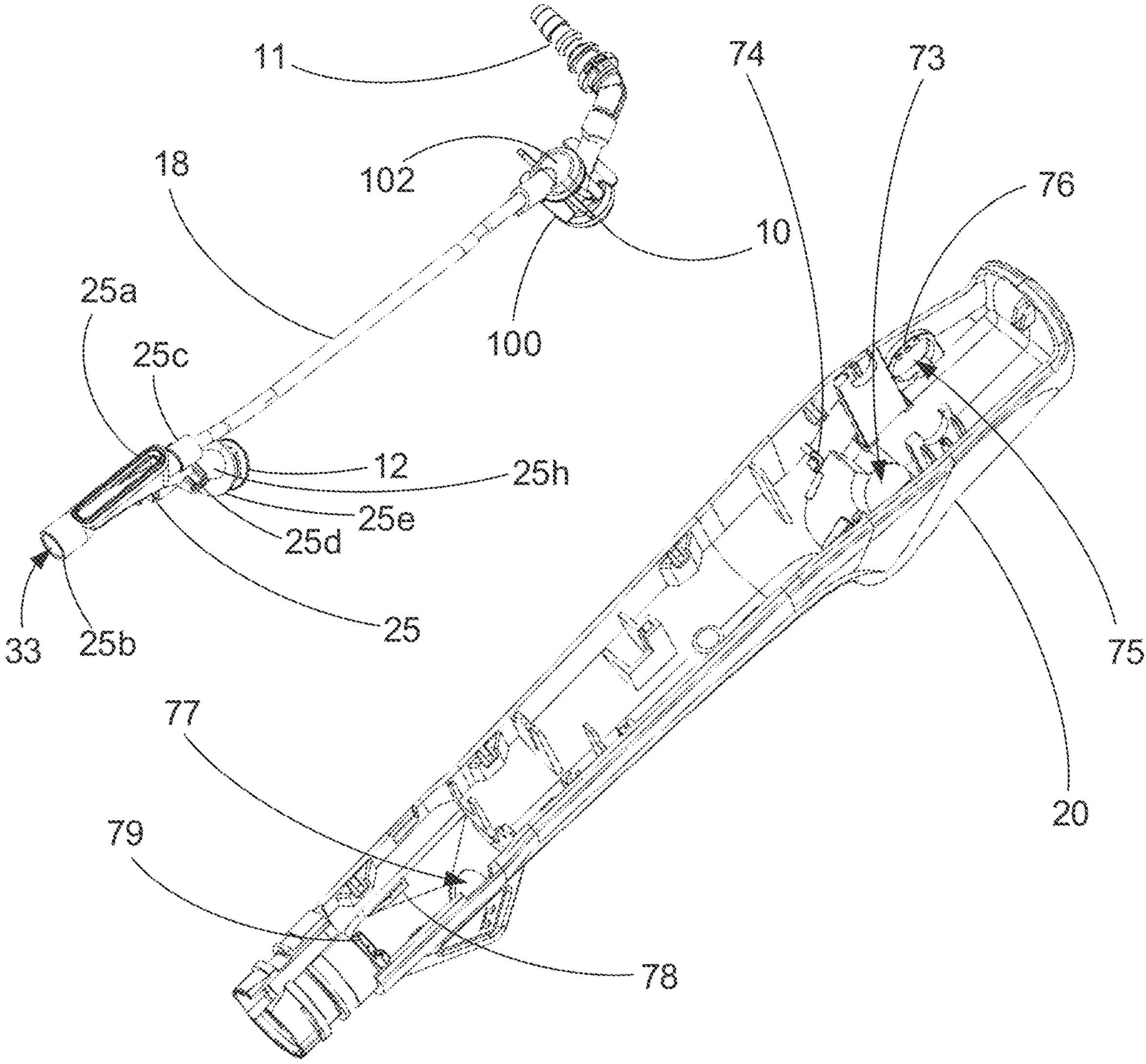
Figures 5, 7:
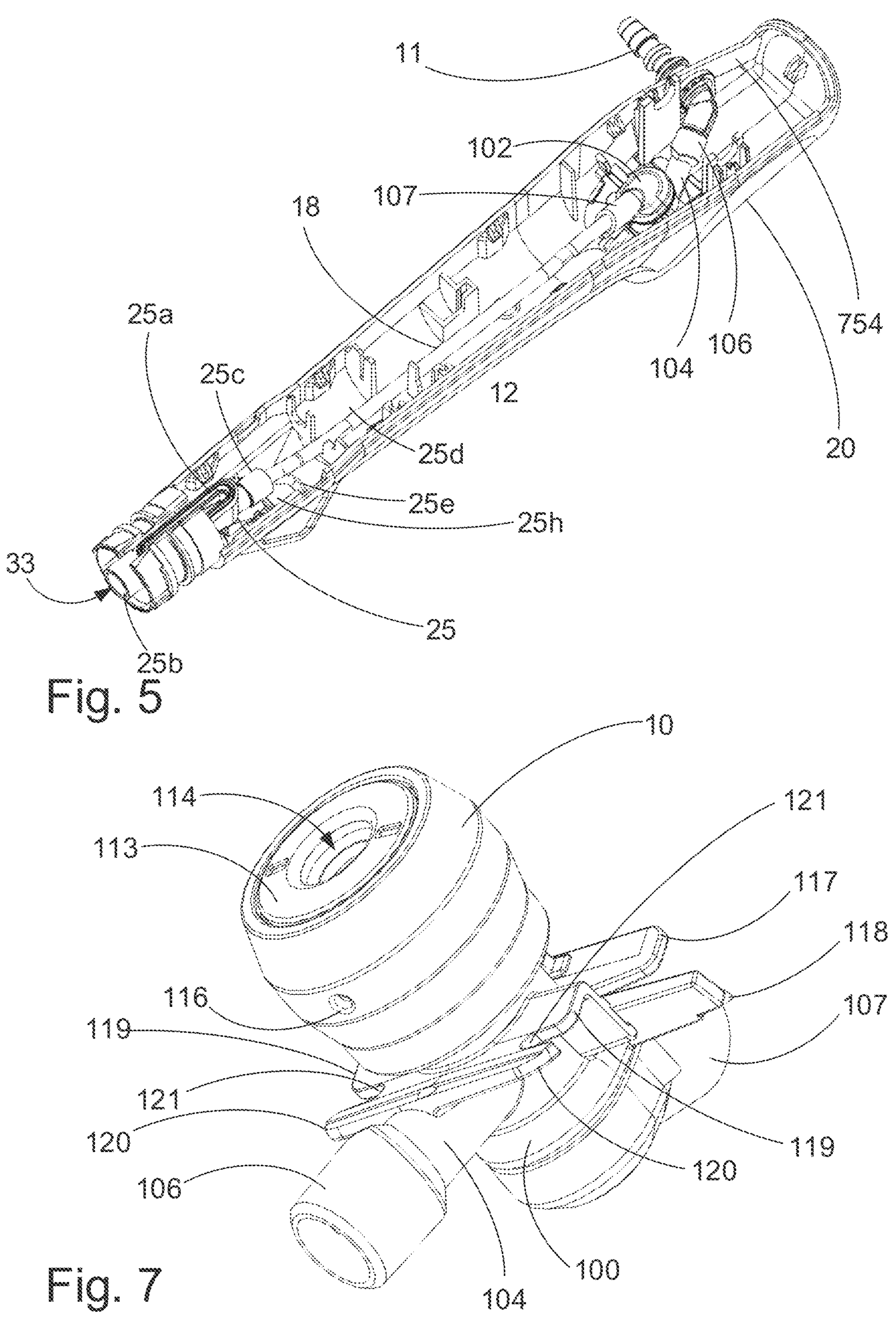
Figure 6:
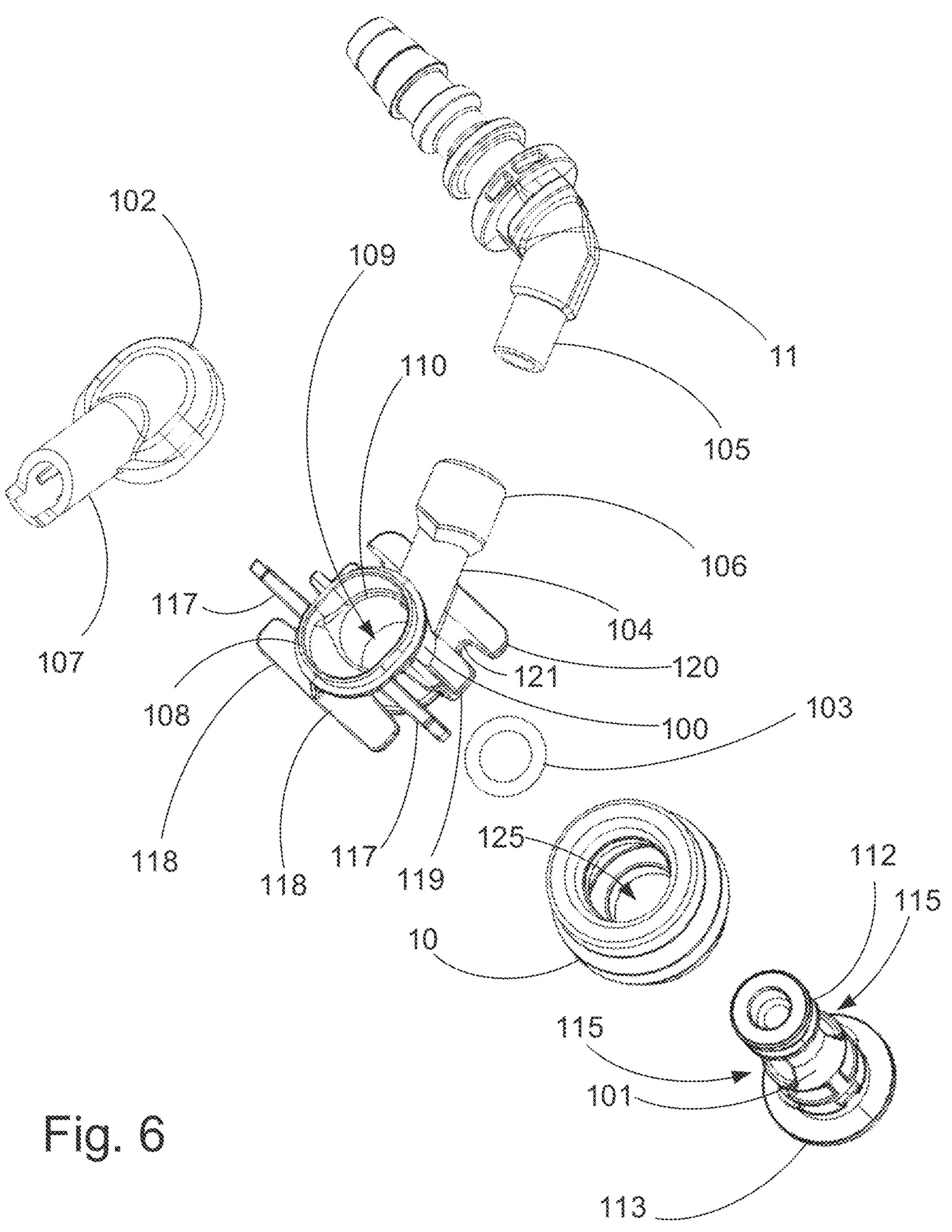
Figure 8:
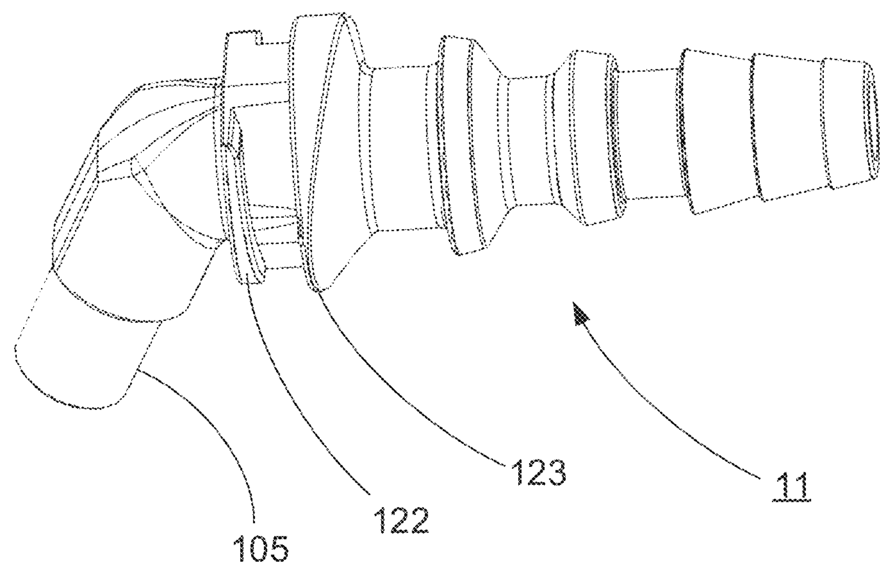
Figure 9:
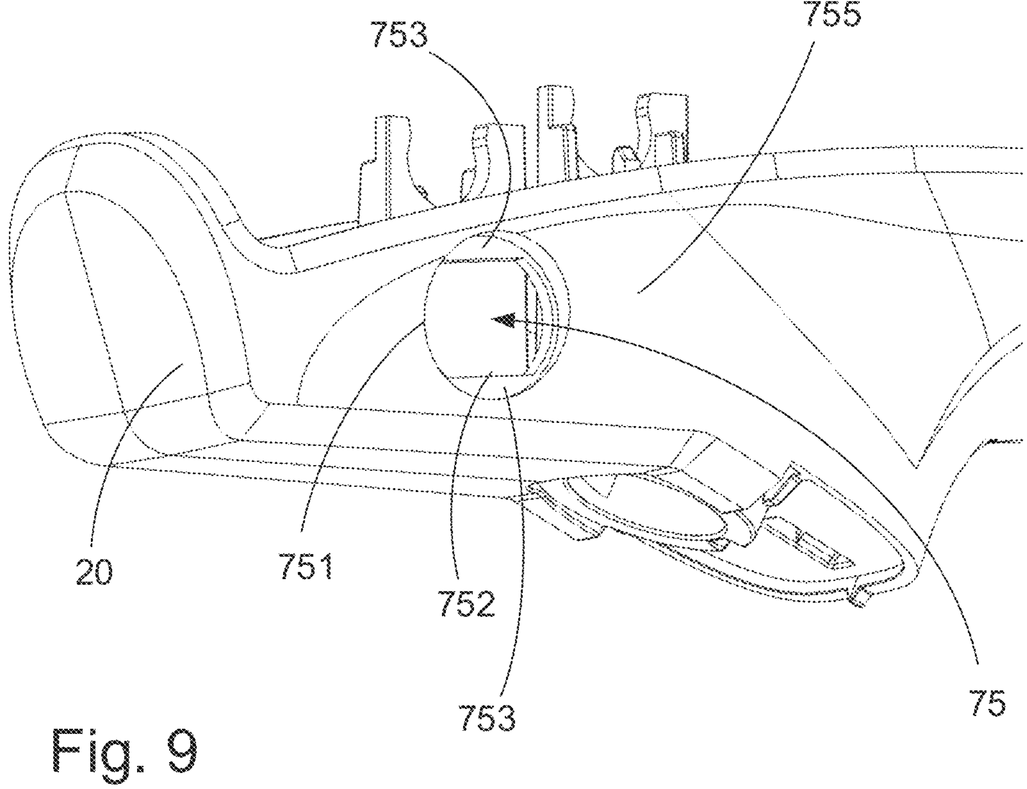
Figures 10, 11:
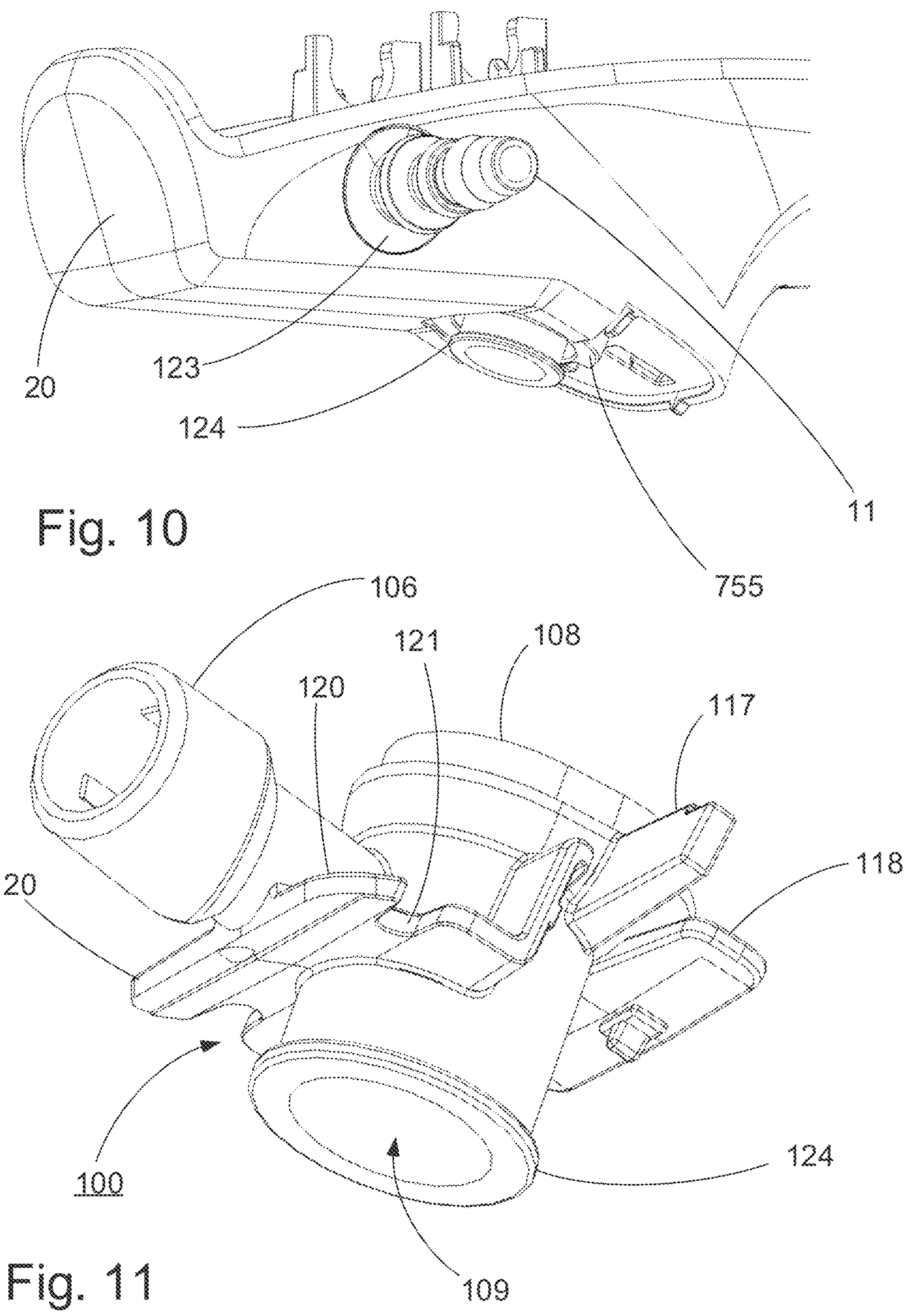
Figure 12:
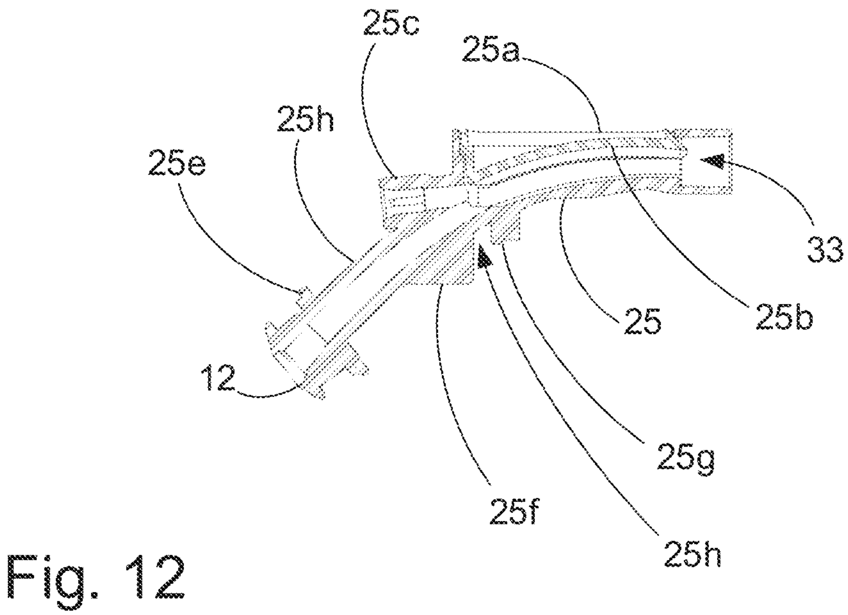

The disclosure will now be made in greater details based on non-limiting exemplary embodiments and with reference to the drawings, on which:

FIG. 1 shows a system comprising an endoscope according to the disclosure and a display device to which the endoscope may be connected, FIG. 2 shows an exploded view of the endoscope of the system in FIG. 1, FIG. 3 shows an exploded view of the handle part of the endoscope of FIG. 2 in greater detail and together with a connection cable, FIG. 4 shows an exploded view of the handle housing part and the assembled valve and suction channel assembly, FIG. 5. shows handle housing part and the assembled valve and suction channel assembly of FIG. 4 joined together, FIG. 6 shows an exploded view of the valve assembly from, FIG. 7 shows the assembled valve assembly of FIG. 6 from a different angle, FIG. 8 shows a detailed view of the suction connector, FIG. 9. shows a detail of the handle housing, FIG. 10 shows the detail of the handle housing of FIG. 9 with the suction connector part and the valve housing main body mounted, FIG. 11 shows the valve housing main body in isometry, and FIG. 12 shows a cross-section of the Y-junction of the suction channel assembly.

Turning first to FIG. 1 a system comprising an endoscope 1 and a display unit 2 is shown. The endoscope 1 may be connected to the display unit 2 by means of a cable 3 with a suitable connector 4. The endoscope 1 is preferably disposable i.e. intended to be thrown away after use on one single patient, whereas the display unit 2 may be used multiple times with different reusable endoscopes. The endoscope is an insertion endoscope comprising a handle 5 at the proximal end, and an insertion cord 6 extending from the handle 5 towards the distal end of the endoscope 1. At the distal end of the insertion cord 6 a bending section which may be controlled by an operating means 8 is provided. As can be seen from FIGS. 2 and 2*b* the bending section comprises a bending section body 7 beneath a flexible cover 7*a*. In turn at the distal end of the bending section 7 a tip housing 9 with the image capture device, lenses, illumination, the distal port of a working and/or suction cannel etc. of the endoscope is provided. At the distal end the working channel will normally double as both working channels for tools and suction channel. The handle 5 normally also comprises a suction activation button comprising an external valve cap 10 forming a push-button for activating the suction though the suction channel to an external vacuum source (not shown) via a suction connector 11. The handle may also have a tool insertion port 12 (cf. FIG. 2) with a cap 12*a* for the insertion of an external tool through the handle and the working channel so as to emerge from the distal working channel port at the tip housing 9. Also, the handle 5 may be provided with buttons for activation electrical switches 13 controlling function of the image capture, such as taking of still images. In accordance with the present disclosure the insertion cord 6 may be rotated with respect to the handle 5 by manually gripping and turning a gripping surface 14 associated with a coupling mechanism which will be describe below.

Turning now to FIG. 2 the components of the exemplary embodiment of the endoscope 1 are shown in exploded view. In FIG. 3 the components relating to the handle 5 and the valve and connector assembly accommodated in the handle.

The purpose of the valve and connector assembly is to, upon command, provide suction through the endoscope 1 from an entry port in a tip housing 8 or the like at the distal end of an insertion cord 6 to an external vacuum source (not shown) connected to a suction connector 11 in the handle 5.

In the illustrated embodiment, this is provided through a series of components devised so that they are easy to assemble. Starting from the tip housing 9 with the entry port, the tip housing 9 also has a passage to which a working channel tube 15 doubling both as a passage for suction and for the introduction of tools through is connected, preferably by means of an adhesive. The working channel tube 15 is connected to the distal end of a connection member 28, also preferably by means of an adhesive. The proximal end of the connection member 28 is provided with an O-ring 29 or other sealing member engaging the inside of a bore 33 in the distal end of a Y-junction body 25, so as to provide part of a rotary coupling between the insertion cord and the handle. Not all endoscopes have this rotary function allowing the insertion cord 6*a* to be rotated with respect to the handle. Accordingly, if such a function is not needed, the working channel tube 15 could be connected directly to the distal end of the Y-junction body 25, e.g. adhered directly in he bore 33. The Y-junction body 25 may be provided integrally, but preferably provided as two part i.e. comprising the main Y-junction body 25 and a lid 25*a* adhered thereto. The lid preferably comprises a curved inner surface 25*b* serving to guide a tool inserted through a tool insertion port 12 at one branch 25*h* of the Y-junction body 25 smoothly into the working channel tube 15. The Y-junction body 25 further comprises a second branch 25*c* to which the distal end of a suction tube 18 is connected, preferably also by means of an adhesive. The suction tube 18 runs along the majority of the length of the handle to a valve and suction connector assembly to which it is connected, also at this point preferably my means of an adhesive.

The valve and suction connector assembly is shown in exploded view in FIG. 6. The valve and suction connector assembly comprises a suction connector part 11 adapted to be mounted in the wall of a handle housing part 20, a valve housing main body 100, a plunger 101, a valve housing lid 102, and may also comprise a sealing member 103, and a valve cap 10 providing together with the plunger 101 a push-button for activating the valve. The valve housing main body 100 is preferably made as a single-piece item. In particular, but not necessarily, made from a transparent plastic material by injection moulding. Likewise, the valve housing lid 102 is also a single-piece item. In particular, but not necessarily, also made from a transparent plastic material by injection moulding, e.g. using the same transparent plastic material as used for the valve housing main body 100.

The valve housing main body comprises an exit pipe 104 adapted to fit a first end 105 the suction connector part 11, e.g. by means of a pipe socket 106 in which the first end 105 of the suction connector part 11 may be adhered to the exit pipe 104. An entry pipe 107 is provided on a separate valve housing lid 102. This valve housing lid 102 is adapted to be adhered to a rim 108 around a central passage 109 in a sealing manner. As can be seen the central passage 109 widens towards the valve housing lid to have a somewhat oval cross-section whereas the remainder of the central passage 109 has narrower, preferably circular cross section, i.e. is cylindrical. The exit pipe branches off from this narrower part of central passage 109. The transition between the cylindrical part and the wider oval part of the central passage provides a valve seat 110. In the situation shown in FIG. 7, where the pushbutton valve cap 10 is not operated, i.e. depressed, this valve seat 110 receives the sealing member 103, which is preferably an elastomer O-ring located in a suitable circumferential groove 112 at the inner end of the plunger 101. Inner in this respect meaning with respect to the handle 5. The outer end of the plunger 101 is provided with a flange 113 resting on the valve cap 10, as can be seen in the view of FIG. 7, e.g. accommodated in a recess in the end surface, so that the plunger 101 is biased outwardly from the handle housing part against which the valve cap 10 rests. The push-button valve cap 10 is preferably made of an elastomer material and so, by the elastic properties, pulls the sealing member into engagement with the valve seat 110 thus sealing the fluid path from the entry pipe 107 to the suction connector part 11 and on to the vacuum source. The valve cap 10 comprises an inward protrusion such as a circumferential bead, engaging a valve cap engagement surface such as in a recess provided in the valve housing main body 100 or preferable below a flange 124 provided on the valve housing main body 100, so as to retain the valve cap 10 in place.

As can be seen from FIG. 7, the flange 113 of the plunger 101 surrounds a central opening 114. This central opening 114 is in communication with one or more crosswise passages 115 allowing false air to be drawn though the connector and valve assembly but the vacuum source when the push-button valve cap 10 is not activated, i.e. not depressed. Depressing it with a finger will close this passage for false air, and at the same time move the sealing member 103 our of engagement with the valve seat 110, allowing fluid to pass from the distal end of the insertion cord **6*a* via the entry pipe 107 to the suction connector 11 and towards the vacuum source. A small bleeding vent 116 may be provided in order not to trap air below the push-button valve cap 10** that could obstruct the depressing thereof.

The valve housing main body 100 is mounted in a valve accommodation passage interconnecting the interior of the handle and an external wall surface of the handle, in the illustrated embodiment provided as an aperture 73 in the wall of a handle housing part 20. As can be seen, in the illustrated embodiment a part of the valve housing main body 100 is accommodated in the valve accommodation passage, so that the valve accommodation passage surrounds a middle part of the valve housing main body 100 accommodated therein, so that the valve housing main body extends over the exterior surface of the handle housing part. As can be seen from FIG. 10, the valve housing main body located 100 in an aperture 73 in the wall of a handle housing part 20 extends so much over the handle housing part 20 that the recess for retaining the valve cap 10 is formed between the flange 124 and the external wall surface of the handle housing part 20. The valve housing main body 100 is preferably adhered to the inner wall of the handle housing part 20. The valve housing main body comprises a number of integrally formed laterally projecting tabs 117, 118, 119, 120 preferably arranged as mirror image pairs. The tabs may serve as adhesion surfaces and/or as positioning means to secure the position with respect to the handle housing part before the adhesive is cured. The adhesive used is preferably an UV curable adhesive, and accordingly the valve housing main body 100 including the integral tabs 117, 118, 119, 120 is made of a transparent plastic material, to allow ultraviolet light to pass through the tabs to the adhesive. The tabs are adapted to the inner shape of the handle housing part and may include an angled tab 119. Cut outs 121 in or between tabs may also be provided.

When in the correct position, the tabs 117 will be located beyond a pair of cam surfaces 74 provided as part of the inner side wall of the valve housing main body 20. With the tabs 117 in the proper location the remainder of the tabs 118, 119, 120 will engage the adhesive provided thereon with the inner surface of the handle housing part 20 and allowing the valve housing main body 100 to be firmly secured to the handle housing part 20 once the adhesive is cured.

The assembly procedure of getting the valve housing main body 100 into the correct position is facilitated by the design of the suction connector part 11. As can best be seen in FIG. 8, the suction connector part 11 comprises to axially spaced flange parts, viz. an inner flange part 122 and an outer flange part 123 adapted to a passage 75 provided in the side wall of the handle housing part 20. The passage 75 is a through passage between the internal surface 754 of the handle housing part 20 and the exterior beyond the external wall surface 755. As can best be seen from FIG. 9, the passage has a stepwise transition from circular cross-section 751 at the outer surface to an oblong somewhat oval cross-section 751 at the inner surface. The diameter of the outer flange part 123 is adapted to fit within the circular cross-section 751 but the diameter is larger than both the length and width of the oblong inner flange part 122, so that it cannot pass though oblong cross-section 752 the passage 75. The outer dimensions, i.e. length and width of the oblong inner flange part 122 are slightly smaller than the oblong cross-section 752 of the passage 75 but otherwise matches it. Thus, if correctly orientated the inner oblong flange part 122 can be passed through the oblong cross-section part 752 of the passage 75 to the inside of the handle housing part 20. It may then be turned to an orientation preventing withdrawal through the oblong cross-section part 752 and hence out of the passage 75. To ensure engagement in this position the inner flange 122 is preferably slightly wedge-shaped allowing it to frictionally and elastically engage a number of bosses 76 of differing heights provided on inside wall of the handle housing part 20, when it is turned. When turning the suction connector part 11 using the first end 105 as a lever, the shelves 753 formed on either side of the oval cross-sectional part 752 at the transition to the circular cross-sectional part 751, will be firmly caught and clamped between the oblong inner flange 122 and the outer flange part 123.

If, according to the disclosure, the first end 105 the suction connector part 11, has been inserted into the pipe socket 106 this turning of the suction connector part 11 using the first end 105 as a lever will swing the valve housing main body 100 into the desired position in aperture 73. During this swing motion, the tabs 117 will slide along the cam surfaces 74 and eventually engage beyond them. When sliding along the cam surfaces 74 the elastic tabs 117 aid in the alignment with the aperture 73 provided for the valve assembly in the handle housing part 20. This therefore secures desired position in which the valve housing main body 100 is to be adhered to the inner wall of the handle housing part 20. Likewise, the pipe joint 106 and the first end of the suction connector part 11, may be permanently joined and sealed by curing and adhesive introduced between the two parts. This adhesive may also be UV curable.

The valve housing lid 102 may have been placed on and adhered on top of the valve housing main body 100 before the latter is swung into place or this may be done subsequently, e.g. as the next step in the assembly process. In any case, the valve housing lid 102 has an oval shape matching that of the rim 108 of the valve housing main body, so that the correct orientation of the entry pipe 107 towards the distal end of the endoscope 1 is readily achieved.

The proximal end of the suction tube 18 may then be inserted into the entry pipe 107 where it may be secured and sealed using an adhesive, preferably also an UV curable adhesive. Compared to the valve housing lid 102 and the valve housing main body 100, the material of which the suction tube is made may be relatively flexible, so that inserting the proximal end into the entry pipe is not a problem, even if that distal end has already been joined to the second branch 25*c* of the Y-junction body 25.

The Y-junction body 25 is inter alia accommodated and held within the handle housing part by mean of a pair of transversely protruding arms 25*d* which when the Y-junction body 25 is inserted into handle housing part 20 with the tool entry port 12 extending through the a suitable hole 77 in the handle housing part 20 snaps into engagement with a pair of protrusions 78 arranged opposite each other on the inner wall of the handle housing part 20. Once snapped into engagement, the first branch 25*b* of the Y-junction body 25 rests on a trestle 79 to which it may be adhered using e.g. UV curable adhesive. To secure the position with respect to the trestle 79 the Y-junction body 25 comprises a rib 25*f* and a block 25*g* separated by a gap 25*h* adapted in width to the trestle 79. Accordingly, the Y-junction body 25 as well as the lid 25*a* are both preferably made of a transparent plastic material. The lid 25*a* is preferably moulded as a through to keep variations in wall thicknesses down and thus facilitate an injection moulding process for the manufacture thereof. The Y-junction body 25 may furthermore comprise a flange 25*e* surrounding the entry port branch and adapted to be adhered to the inside wall of the handle housing part surrounding the hole 77.

At an appropriate stage in the assembly process the push-button valve cap 10 and the plunger 101 with the sealing member 103 is fitted to the valve assembly, which sealing member is preferably an elastomer O-ring located in a suitable circumferential groove 112 at the inner end of the plunger 101. This is done from the outside of the handle housing part 20. The plunger 101 is inserted into the central aperture 125 of the valve cap 10 so that the flange 113 rest on outer end of the valve cap 10. Before doing so, the sealing member 103, e.g. an O-ring is fitted. The end of the plunger 101 with the sealing member 103 is then pressed through the narrower cylindrical part of central passage 109 and into the wider part, where the sealing member 103 expands of its original shape and size behind the valve seat 110. Upon release of the valve cap 10, the elasticity of the valve cap 10 returns it to its original shape. Since the flange 113 rests on the valve cap 10, the plunger 101 is pulled outward from the external wall surface 755 when the valve cap 10 returns to its original shape, and the sealing member 103 is pulled consequently pulled back into engagement with the valve seat 110.

I claim:

1. An endoscope comprising a handle and an insertion cord, said handle comprising a handle housing part, an interior, and a valve and suction connector assembly, said handle housing part including a wall, the wall comprising an internal wall surface, an external wall surface, and a valve accommodation passage provided as an aperture in the wall, the aperture extending between the external wall surface and the internal wall surface, and said valve and connector assembly comprising a suction connector part, a valve housing main body, a plunger, and a valve housing lid, wherein said valve housing main body is accommodated in said valve accommodation passage so as to extend from the interior of the handle through said valve accommodation passage and beyond said external wall surface, wherein the plunger is so accommodated in the valve housing main body that the plunger extends from the interior of the handle through said valve accommodation passage and beyond said external wall surface, and wherein the valve housing main body comprises at least one pair of laterally extending elastic tabs retained in position by cam surfaces provided on the internal wall surface.

2. The endoscope of claim 1, the valve and suction connector assembly further comprising a valve cap, wherein the plunger extends further beyond the external wall surface than the valve housing main body, wherein the valve housing main body comprises a valve cap engagement surface, wherein said valve cap engagement surface comprises a flange, wherein the plunger comprises a valve cap engagement flange adapted to retain the valve cap in engagement with the plunger.

3. The endoscope of claim 1, wherein the valve housing main body comprises a valve cap engagement surface.

4. The endoscope of claim 3, wherein said valve cap engagement surface comprises a flange.

5. The endoscope of claim 1, wherein the plunger comprises a valve cap engagement flange adapted to retain a valve cap in engagement with the plunger.

6. The endoscope of claim 1, where said valve housing lid is adhered to said valve housing main body.

7. The endoscope of claim 1, wherein said valve housing main body comprises a valve seat surface and said plunger comprises a sealing member adapted to engage said valve seat surface.

8. The endoscope of claim 7, wherein said sealing member is biased towards engagement with said valve seat surface by an elastomeric valve cap providing a push-button valve cap arranged on an exterior of said handle housing part.

9. The endoscope of claim 1, wherein said plunger comprises a passage in fluid communication with an exterior of the handle housing part.

10. A system comprising a display device and the endoscope of claim 1, the endoscope being connectable to said display device.

11. An endoscope comprising a handle and an insertion cord, said handle comprising a handle housing part, an interior, and a valve and suction connector assembly, said handle housing part including a wall, the wall comprising an internal wall surface, an external wall surface, and a valve accommodation passage provided as an aperture in the wall, the aperture extending between the external wall surface and the internal wall surface, and said valve and connector assembly comprising a suction connector part, a valve housing main body, a plunger, and a valve housing lid, wherein said valve housing main body is accommodated in said valve accommodation passage so as to extend from the interior of the handle through said valve accommodation passage and beyond said external wall surface, and wherein the plunger is so accommodated in the valve housing main body that the plunger extends from the interior of the handle through said valve accommodation passage and beyond said external wall surface, wherein the endoscope further comprises a suction channel tube and a suction port at a distal end of the insertion cord, wherein the valve housing lid comprises an entry pipe connected to the suction channel tube, wherein the suction channel tube is in fluid communication with the suction port at the distal end of the insertion cord, wherein the valve housing main body comprises an exit pipe connected to said suction connector part, wherein the suction connector part is accommodated in said wall, and wherein said suction connector part comprises an oblong engagement flange in frictional engagement with said wall.

12. The endoscope of claim 11, wherein the valve housing main body comprises at least one pair of laterally extending elastic tabs retained in position by cam surfaces provided on the internal wall surface.

13. The endoscope of claim 12, wherein the elastic tabs are further secured in position by an adhesive provided between said elastic tabs and the internal wall surface.

14. An endoscope comprising a handle and an insertion cord, said handle comprising a handle housing part, an interior, and a valve and suction connector assembly, said handle housing part including a wall, the wall comprising an internal wall surface, an external wall surface, and a valve accommodation passage provided as an aperture in the wall, the aperture extending between the external wall surface and the internal wall surface, and said valve and connector assembly comprising a suction connector part, a valve housing main body, a plunger, and a valve housing lid, wherein said valve housing main body is accommodated in said valve accommodation passage so as to extend from the interior of the handle through said valve accommodation passage and beyond said external wall surface, wherein the plunger is so accommodated in the valve housing main body that the plunger extends from the interior of the handle through said valve accommodation passage and beyond said external wall surface, wherein the valve and suction connector assembly further comprises a valve cap, wherein the valve housing main body comprises a valve cap engagement surface, wherein said valve cap engagement surface comprises a flange, and wherein the plunger comprises a valve cap engagement flange adapted to retain the valve cap in engagement with the plunger.

15. An endoscope comprising:

a handle including a handle housing part, an interior, and a valve and suction connector assembly; and an insertion cord;

said handle housing part including a wall comprising an internal wall surface, an external wall surface, and a valve accommodation passage provided as an aperture in the wall, the aperture extending between the external wall surface and the internal wall surface, and said valve and connector assembly comprising a suction connector part, a valve housing main body, a plunger, a valve cap, and a valve housing lid, wherein said valve housing main body comprises a valve cap engagement surface, said valve cap engagement surface comprises a flange, and said valve housing main body is accommodated in said valve accommodation passage so as to extend from the interior of the handle through said valve accommodation passage and beyond said external wall surface, and wherein the plunger comprises a valve cap engagement flange configured to retain the valve cap in engagement with the plunger and the plunger is so accommodated in the valve housing main body that the plunger extends from the interior of the handle through said valve accommodation passage and beyond said external wall surface further than the valve housing main body.

16. The endoscope of claim 15, wherein the endoscope further comprises a suction channel tube and a suction port at a distal end of the insertion cord, wherein the valve housing lid comprises an entry pipe connected to the suction channel tube, wherein the suction channel tube is in fluid communication with the suction port at the distal end of the insertion cord, wherein the valve housing main body comprises an exit pipe connected to said suction connector part, wherein the suction connector part is accommodated in said wall, and wherein said suction connector part comprises an oblong engagement flange in frictional engagement with said wall.

17. The endoscope of claim 15, wherein the valve housing main body comprises at least one pair of laterally extending elastic tabs retained in position by cam surfaces provided on the internal wall surface.

18. An endoscope comprising:

a handle including a handle housing part, an interior, and a valve and suction connector assembly; and an insertion cord including a suction channel tube and a suction port at a distal end of the insertion cord;

said handle housing part including a wall comprising an internal wall surface, an external wall surface, and a valve accommodation passage provided as an aperture in the wall, the aperture extending between the external wall surface and the internal wall surface, and said valve and connector assembly comprising a suction connector part, a valve housing main body, a plunger, a valve cap, and a valve housing lid, wherein said valve housing main body comprises a valve cap engagement surface, said valve cap engagement surface comprises a flange, and said valve housing main body is accommodated in said valve accommodation passage so as to extend from the interior of the handle through said valve accommodation passage and beyond said external wall surface, and wherein the plunger comprises a valve cap engagement flange configured to retain the valve cap in engagement with the plunger, wherein the valve housing lid comprises an entry pipe connected to the suction channel tube, wherein the suction channel tube is in fluid communication with the suction port at the distal end of the insertion cord, wherein the valve housing main body comprises an exit pipe connected to said suction connector part, wherein the suction connector part is accommodated in said wall, and wherein said suction connector part comprises an oblong engagement flange in frictional engagement with said wall.

19. The endoscope of claim 18, wherein the valve housing main body comprises at least one pair of laterally extending elastic tabs retained in position by cam surfaces provided on the internal wall surface.

20. The endoscope of claim 19, wherein the elastic tabs are further secured in position by an adhesive provided between said elastic tabs and the internal wall surface.

* * * * *